United States Patent [19]

Tomecek

[11] 4,112,923
[45] Sep. 12, 1978

[54] ANTONOMIC TRANSCUTANEOUS AFFECT DEVICE

[76] Inventor: Jerry J. Tomecek, 10730 Kennicott Trail, Brighton, Mich. 48116

[21] Appl. No.: 717,254

[22] Filed: Aug. 24, 1976

[51] Int. Cl.² .............................................. A61N 1/00
[52] U.S. Cl. .................................. 128/1.3; 128/2.1 Z; 128/362; 128/395; 128/405; 128/419 R
[58] Field of Search ................................ 128/1.3–1.5, 128/1 C, 2.1 C, 2.1 Z, 2.1 R, 24.1, 362, 395–398, 404, 405, 419 R, 421, 422

[56] References Cited

U.S. PATENT DOCUMENTS

| | | | |
|---|---|---|---|
| 1,936,405 | 11/1933 | Mueller | 128/1.3 X |
| 2,706,979 | 4/1955 | Wallace | 128/1.4 |
| 2,830,578 | 4/1958 | Groff | 128/419 R |
| 3,207,161 | 9/1965 | Dietz | 128/404 |
| 3,255,753 | 6/1966 | Wing | 128/421 |
| 3,648,708 | 3/1972 | Haeri | 128/422 |
| 3,735,756 | 5/1973 | Richards et al. | 128/421 X |
| 3,773,049 | 11/1973 | Rabichev et al. | 128/362 |
| 3,894,532 | 7/1975 | Morey | 128/422 X |
| 3,900,034 | 8/1975 | Katz et al. | 128/395 |
| 4,019,510 | 4/1977 | Ellis | 128/421 X |

OTHER PUBLICATIONS

Fridlund et al., "An Inexpensive . . . Stimulator", Behavior Research Methods & Inst., Feb. 1976, vol. 8, No. 1, pp. 21–23.

*Primary Examiner*—Robert W. Michell
*Assistant Examiner*—Lee S. Cohen
*Attorney, Agent, or Firm*—Basile and Weintraub

[57] ABSTRACT

A device for effectuating an automatic transcutaneous affect by applying energy to a living organism includes a self-contained power supply disposed in a housing. A probe circuit is utilized to detect points of high and/or low resistance in the organism. When such points are realized an audio emission begins thereby signalling the point. The device, also, includes a treatment circuit which applies either electrical, light or magnetic energy to the detected point. The present device utilizes interlocking logic circuits to preclude more than one mode being carried out at any one time.

12 Claims, 15 Drawing Figures

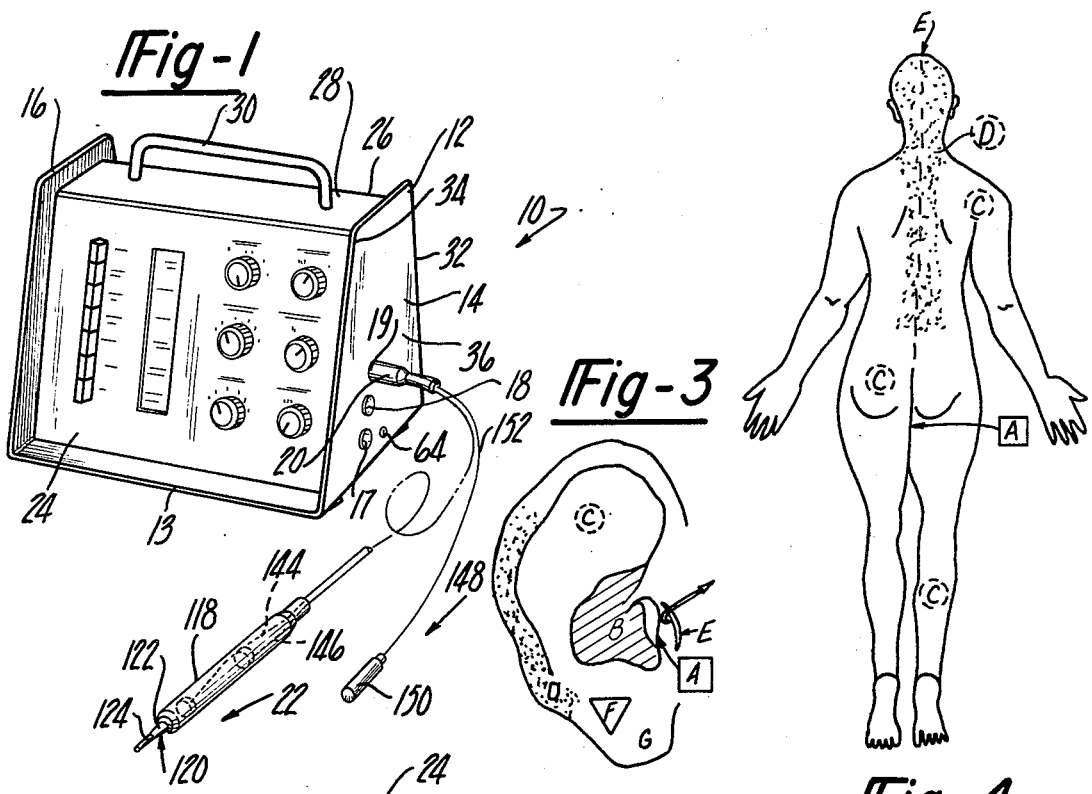
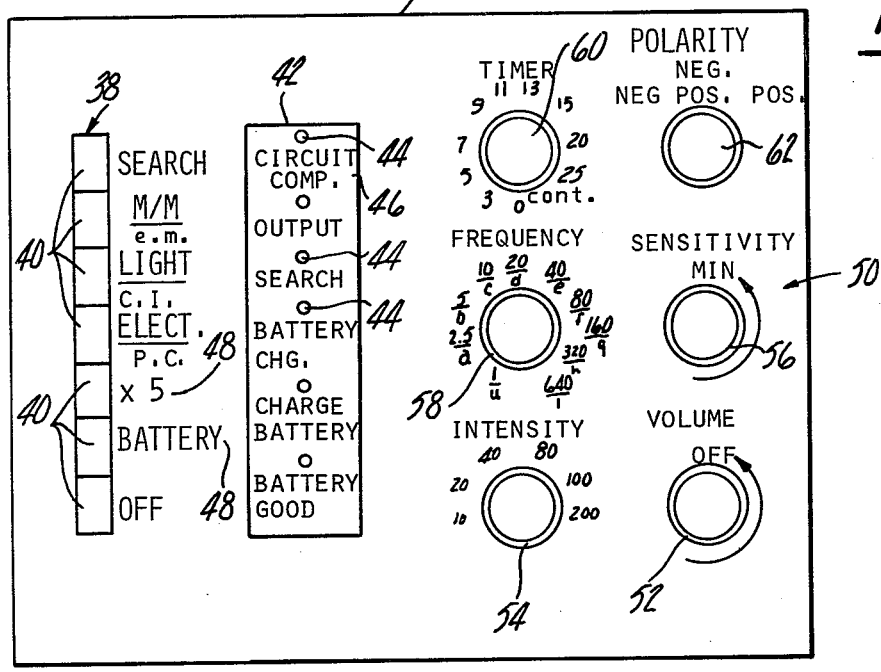

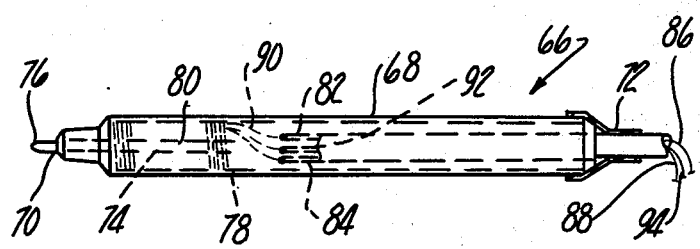
*Fig-6*
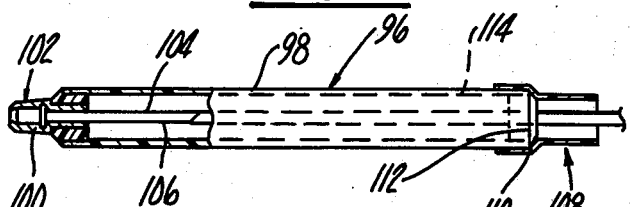
*Fig-7*
| CONVERSION TABLE | |
|---|---|
| LETTER | FREQUENCY |
| y | 1 |
| a | 2.5 |
| b | 5 |
| c | 10 |
| d | 20 |
| e | 40 |
| f | 80 |
| g | 160 |
| h | 320 |
| j | 640 |
*Fig-5*
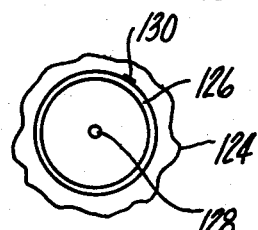
*Fig-8*
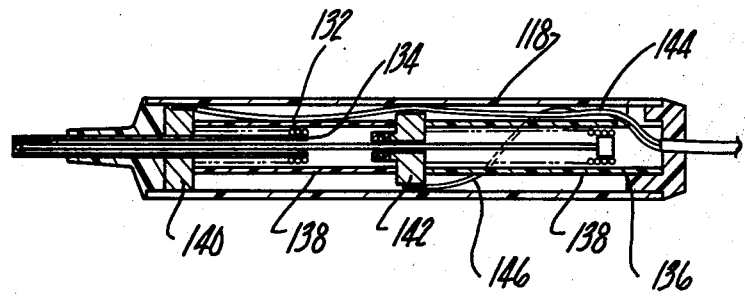
*Fig-9*
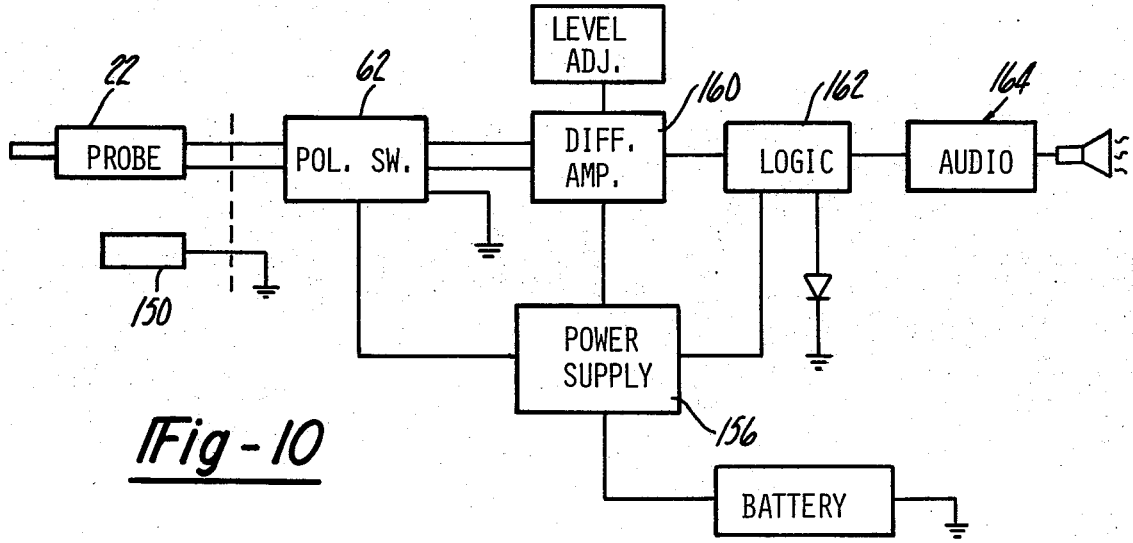
*Fig-10*

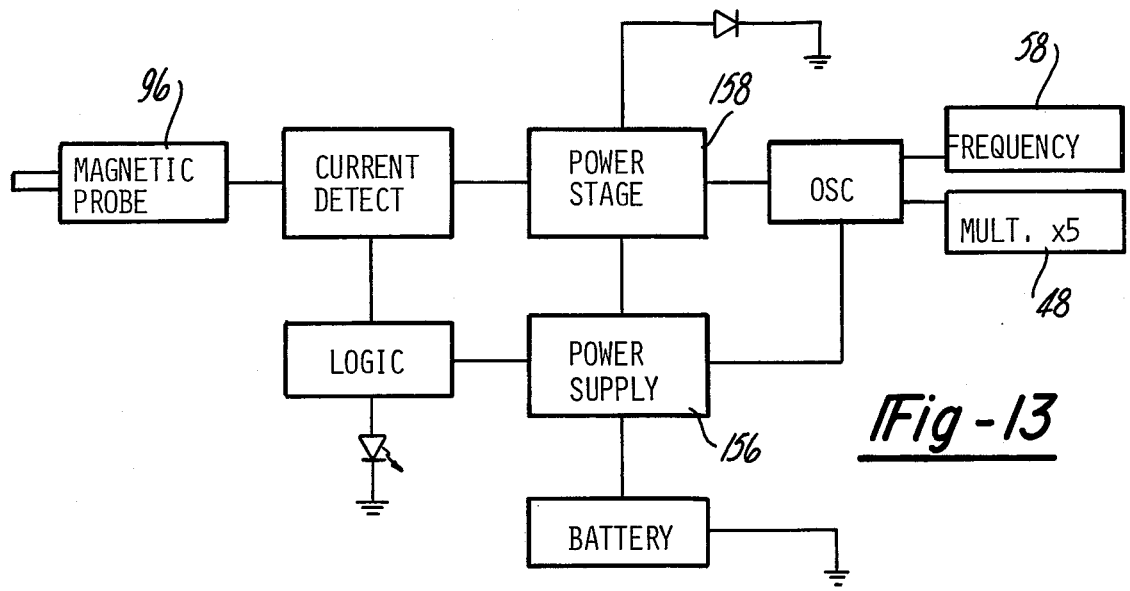
_Fig-13_
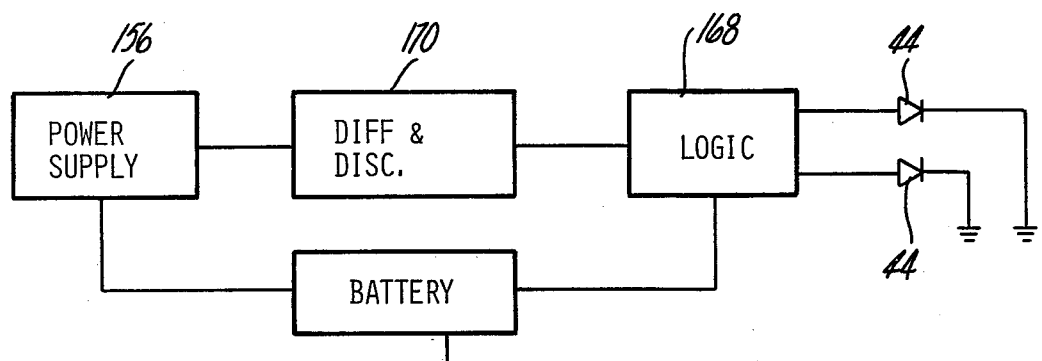
_Fig-14_
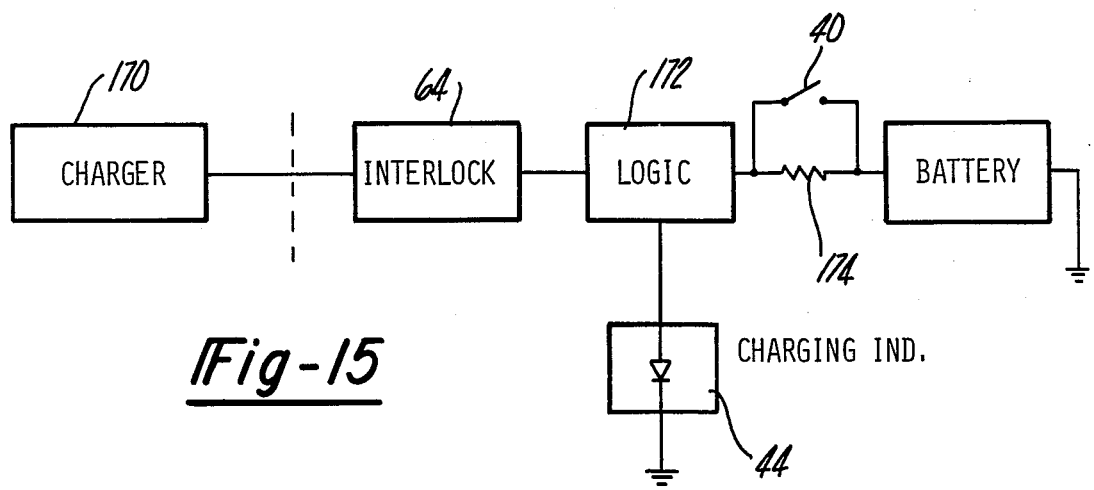
_Fig-15_

ANTONOMIC TRANSCUTANEOUS AFFECT DEVICE

BACKGROUND OF THE INVENTION

1. Field of the Invention

The present invention pertains to treatment devices. More particularly, the present invention pertains to devices for applying energy for the treatment of preselected areas on a living organism. Even more particularly, the present invention concerns devices for effectuating an autonomic transcutaneous affect to a preselected area on a living organism through the application of energy thereto.

2. Prior Art

Around 1960 it was demonstrated by French experimentalists that the physical condition of a living organism, including humans and other animals, was reflected on the subject's ears. The reflection by the ear, as hypothesized and demonstrated, was in inverted fetus in the fetal position.

The physical conditions reflected by the ear are indicated by small areas of electrical resistance which are different from that of the immediate surroundings on the auricle or ear. These small areas, which are referred to as "points," can be of a higher or lower resistance, than the immediate surroundings. Points of high resistance are referred to as positive points and points of low resistance are referred to as negative points.

It has been established heretofore that when the centers of positive points are inundated with electrical pulses having a higher potential at the centers of the points the points return to resistive equilibrance with the surroundings after a period of time. The same is true with respect to negative points upon the application of electrical pulses with a lower potential.

The return of the point to resistive equilibrance causes the organism's body to return to a normal homostatius. It has, also, been established heretofore that the various portions of the ear and, therefore, the body return to homostatius or equilibrance at variant frequencies and intensities of the applied pulses. Furthermore, it has, also, been established that the ear responds to forms of applied energy other than electrical. Thus, homostatius can be achieved through the application of light, heat pressure and magnetic energy to the points.

With respect hereto, it is to be appreciated that it is incumbent to accurately define the points of resistive differentials or imbalance and then to properly apply the correct magnitude of energy thereto to cause or impart homostatius thereto.

The present invention, as will subsequently be described, provides a device with an accurate search mode for determining the points, as well as providing means for treating the point with various forms of energy at the correct frequencies, intensities and times. Furthermore, the present invention provides means for indicating that treatment is being effected.

SUMMARY OF THE INVENTION

In accordance herewith, the present invention provides a device for applying energy to a point of resistive imbalance, as heretofore defined. The device hereof comprises a housing having a plurality of interlocked logic circuit keyboards disposed therewithin. The logic circuits each carry out an individual mode or function. A first circuit defines means for searching out and defining a point with electrical energy; a second circuit defines means for searching out and treating a point with light energy, and a third circuit defines a means for searching out and treating a point with magnetic energy. The outputs of each circuit are interlocked such that only one of such circuits is operable at any one time.

The present device, also, includes means for indicating that the treatment or application of energy to a point is being effectuated. The present device further comprises a source of positive and negative energy for treating both positive and negative points.

Furthermore, the present invention is capable of treating points that vacillate between both positive and negative by providing a positive-negative energy source, whereby the effect is such that the effected point(s) absorb or utilize their correct polarity of pulses.

Also, the present invention comprises a differential probe which searches out a point. The probe is, also, employed to apply the energy to the points detected therewith.

The present invention incorporates therewithin means for varying the frequency, intensity, and polarity of the applied energy.

For a more complete understanding of the present invention reference is made to the following detailed description and accompanying drawing. In the drawing like reference characters refer to like parts throughout the several views in which:

BRIEF DESCRIPTION OF THE DRAWING

FIG. 1 is a perspective view of the device of the present invention with a probe connected thereto;

FIG. 2 is an amplified plan view of the front face of the present device;

FIG. 3 is a plan view of an auricle showing the cartography thereof;

FIG. 4 is a plan view of a person showing the regions thereof which correlate to the regions of the auricle cartographically;

FIG. 5 is a chart depicting the interrelationship between the regions of the auricle or the body and the necessary frequency of the energy to be applied to the points within the region;

FIG. 6 is a cross-sectional view of a differential probe for treating magnetically;

FIG. 7 is a cross-sectional view of a differential probe for treating a point with light;

FIG. 8 is an end view of a bipolar electrical probe;

FIG. 9 is a cross-sectional view of the bipolar electrical probe of FIG. 8.

FIG. 10 is a block circuit diagram for the electrical search of a point;

FIG. 13 is a block circuit diagram depicting the treatment and search mode for use with magnetic energy;

FIG. 14 is a block circuit diagram of the means for indicating the status of the self-contained power supply, and FIG. 15 is a block circuit diagram of the means for charging the power supply.

DESCRIPTION OF THE PREFERRED EMBODIMENTS

Figure 11:
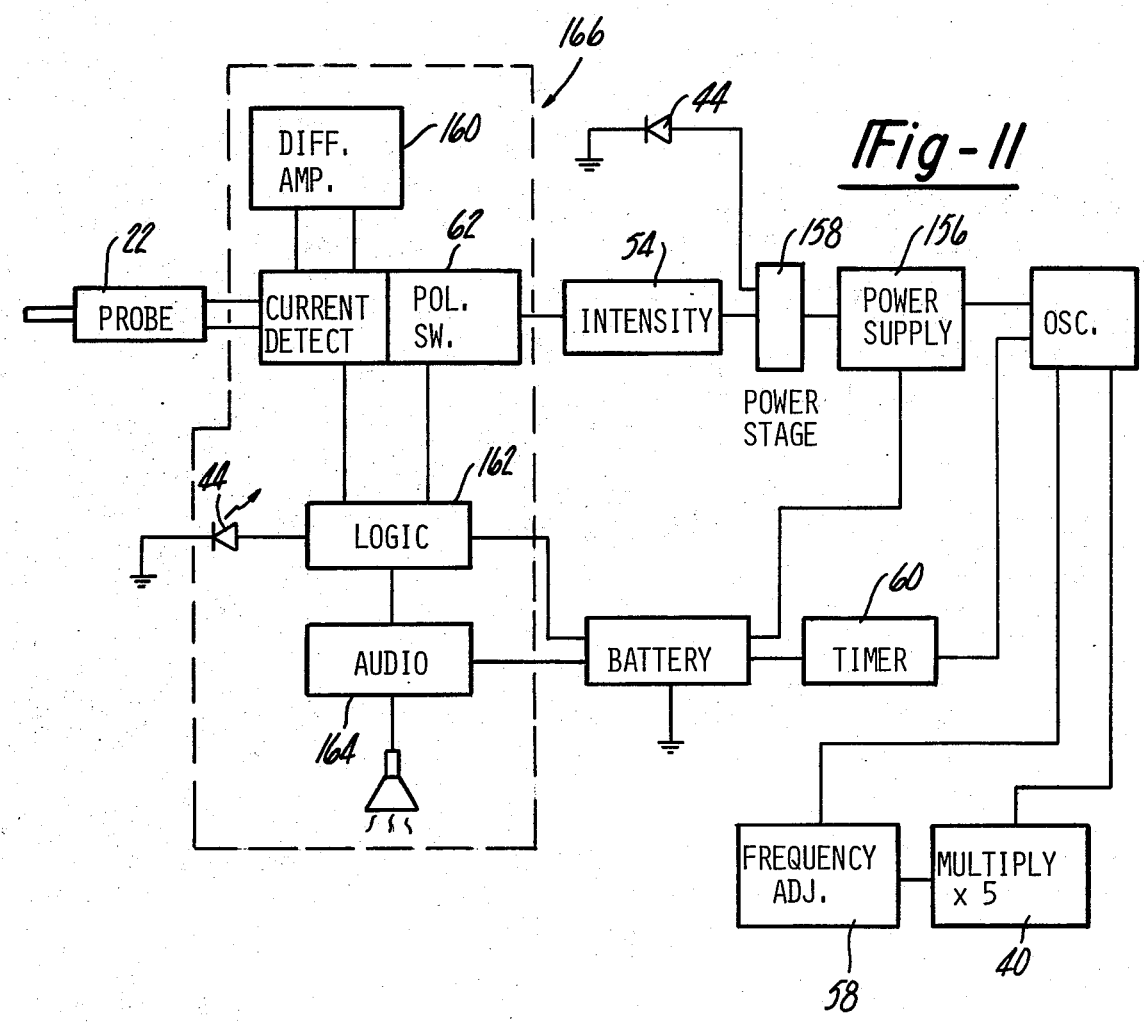
FIG. 11 is a block circuit diagram for the electrical treatment of a point.

Now, and with reference to the drawing, there is depicted, in accordance herewith, a device, generally, inciated at 10 for applying energy to a predetermined point of a living organism to effectuate an autonomic transcutaneous affect (A.T.A). This A.T.A. forces or causes the points to achieve homostatius in the manner heretofore described. In order to facilitate an understanding of the present invention each aspect thereof will be described individually.

THE HOUSING

The device 10 comprises a housing 12 having a bottom wall 13 and a pair of opposed, spaced apart side panels 14, 16. One panel has a plurality of socket jacks 17, 18 and 19 which receive a plug-in socket 20 associated with a probe, generally denoted at 22. The jacks 17, 18 and 19 are in electrical communication with a power supply (not shown) disposed in the housing.

Each one jack is associated with one of the probes contemplated for use herein. With respect hereto, it should be noted that any one probe socket can be physically plugged into any one jack. However, if the wrong socket is plugged into the wrong jack, then, electrical energy will not be delivered to the probe. Therefore, it is necessary hereto that both the proper physical and electrical contact be made between the sockets and the probes in order to render the device operable. Thus, for example, the jack 17 will only electrically and physically communicate with the socket of a light probe; jack 18 will only electrically and physically communicate with an electric probe, etc.

The housing 12, also, comprises a front panel 24 and rear panel 26. The front and rear panels are interconnected by a top wall 28. The front and rear panels as well as the top wall are recessed with respect to the side walls and the bottom wall, as shown. This enables an interlocking cover (not shown) to be fitted over the housing to protect the front panel.

A handle 30 is secured to the top wall 28 to facilitate transporting of the device.

A portion 32 of the rear panel is rotatably hingedly secured, as at 34, to the panel, per se. The hinged portion 32 is rotatable away from the remainder of the panel to provide access into the interior of the housing. A platform 36 traverses the interior of the housing 12 to define a storage shelf. Thus, probes and other appliances can be stored within the housing 12 by opening up the rear panel through rotation of the hinged portion.

Referring specifically to FIGS. 1 and 2, and as hereinbefore noted, the housing 12 comprises a front panel 24. The front panel defines a display board for indicating the various functions carried out by the present invention. The front panel 24 comprises a first column 38 of interlocking push button switching means 40. The switching means are interlocked in a conventional manner such that only one such switching means is actuable at any one time, except in three specific instances. First, the "×5" multiplying circuit is operable at all times to increase the frequencies of the outputs. Thus, the switch 40 thereof can be depressed when any of the other switches are depressed. Secondly, and as will subsequently be detailed, both of the "off" and "×5" switches can be simultaneously depressed to provide a "fast charge" to the battery when the device is in the battery charging mode. Thirdly, the electrical and off can be simultaneously depressed to reconnect a ground or grip associated with the electrical probe, as subsequently described. Each switching means 40 is associated with one of the logic circuits for carrying out a designated function in a manner to be described subsequently.

The front panel, also, comprises a second column 42 which comprises an illumination display. The display indicates the status of the various functions being carried out by the present device. To this end, disposed along the column 42 are a plurality of illuminating means 44. The illuminating means, preferably, comprises a plurality of light emitting diodes (LED's), each one of the plurality being associated with one of the functions. Suitable indicia 46 is disposed and displayed beneath each LED. It is to be noted that each of the switching means 40 has indicia 48 associated therewith to identify the logic circuit actuated thereby.

Also, disposed on the front panel is a switching area, generally denoted at 50. The switching area, comprises a plurality of externally accessible rotatable switching knobs for use in applying energy to an area to be treated. A first switch 52 is used to vary the amplitude of a volume control amplifier utilized in the electrical energy search and treatment. A second switch 54 is utilized to vary, within a fixed position, the current intensity of the output of the electrical energy medium.

The sensitivity control knob 56 is used to regulate the resistivity of the electronic comparator in the logic circuits to bring the comparator to equilibrium with the impedance of the externally measured point.

The frequency control knob 58 is variable over ten frequency ranges to alter the frequency output of the applied energy in accordance with the predetermined frequency to be applied to any one point.

An electronic timer (not shown) is mounted within the interior of the housing. A conventional rotatable dial 60 is utilized to set the timer. The timer is, ordinarily, utilized only with electrical treatment.

As hereinbefore noted, the present invention contemplates the application of positive, negative or positive-negative electrical energy from a bipolar power supply. The power supply is electrically connected to a rotatably switching dial 62 which is employed to select the desired polarity of the power supply output.

It should, also, be noted that a sidewall 14 of the housing 12 is provided with an outlet 64 which is connected to the batteries. The outlet 64 receives the terminal end of a battery charger (not shown) for re-charging the batteries upon their depletion.

THE PROBES

A. The Magnetic Probe

In FIG. 6 there is depicted the magnetic probe, generally, denoted at 66. The probe 66 comprises a housing 68 formed from a non-magnetic and non-conductive material, such as a rigid plastic. Preferably, the housing is formed from an acrylic plastic. The housing 68 has a hollow interior and a bore 70, 72 respectively, at each end thereof. Extending through the housing is a pin 74 formed from a magnetic material such as nickel, iron or the like. The pin 74 has one end thereof extending through the bore 70 and defines the search and treatment end 76 of the probe.

Disposed within the housing proximate the end 76 is a pair of coils 78, 80 which are wrapped around the pin 74. Preferably, there are about 4,400 turns around the pin 74 of number 36 copper wire. The coils are wound in opposite directions around the pin which cooperate to define an unipolar electromagnet. The free ends of the coils are connected, through suitable connectors 82, 84 to electrical lead wires 86, 88. A ground wire 90, also, extends from the coils to a connector 92 which, in turn, is connected to a grounding lead wire 94. The lead wires 86, 88 and 94 have their free ends connected to a socket plug (not shown) which is received by the appropriate jack 17, 18 or 19 (FIG. 1).

B. The Light Probe

In FIG. 7 there is depicted the construction of the light probe utilized for detecting the treating a point, and, generally, denoted at 96.

The probe 96 comprises a plastic housing 98 having a hollow interior. One end of the probe 96 defines a probe tip 100. Disposed within the tip 100 is a light emitting source 102, such as a light emitting diode or other high intensity light source extending from the LED through the interior of the housing are a pair of lead wires 104, 106. The lead wires exit from the rear end 108 of the housing through an aperture 110 formed in an end cap 112 which is press fitted into the rear end of the housing.

Within the interior of the housing, the lead sires are enveloped within a shrink fit tubing 114 disposed within the housing. The tubing 114 defines a sheath for the lead wires.

The free ends of the lead wires are connected to a socket plug in the manner heretofore described.

C. The Bipolar Electrical Probe

In FIGS. 1, 8 and 9, there is depicted the bipolar electrical probe employed in the practice of the present invention and, generally, denoted at 116. The bipolar electrical probe 116, generally, comprises a housing 118 formed from a non-conductive material, such as an acrylic plastic or the like. The housing has a first or front end 120. The front end 120 is provided with a conical tip 122 having a central aperture 124. Disposed within the housing and extending through the aperture 124 are concentric detectors 126, 128, respectively. The outer detector 126 has the portion thereof disposed exteriorly of the housing enveloped with a non-conductive coating 130. The detector 126, per se, is conductive. Furthermore, the detector 126 defines a sheath for the inner detector 128.

As shown clearly in FIG. 9 the outer detector extends into the housing a shorter distance than the inner detector. The portion of the detector 126 disposed in the housing has a biassing means, such as a spring 132, mounted therearound. A circular stop 134 limits expansion of the spring to bias the detector toward the exterior of the probe.

The inner detector 128 is an elongated pin which extends substantially throughout the length of the housing. The end of the detector disposed within the housing has a biassing means, such as a spring 136 mounted therearound to bias the detector towards the exterior of the housing through the aperture 124. The detector 128 is formed from a conductive material.

The portions of the detectors disposed within the housing 118 are mounted within an inner housing 138 formed from a non-conductive material. The inner housing 138 is concentric with the housing 118. The inner housing has a pair of spacers 140, 142, respectively, associated therewith. The first spacer 140 is disposed proximate the front end of the housing and the second spacer 142 is disposed proximate the medial portion of the housing. The spacers are formed from a conductive material and have central apertures formed therethrough. The apertures are dimensioned such that the outer detector contacts the sidewall of the aperture of the first spacer and the inner detector contacts the sidewall of the aperture of the second spacer.

As shown in FIGS. 1 and 9, a pair of lead wires 144, 146 extend from the plug 20 to the housing 118. The lead wires are disposed in the annular space between the inner housing 138 and the outer housing 118. One lead wire is electrically connected to the first spacer and the other wire is electrically connected to the second spacer, to thereby provide electricity to the respective detectors.

As will subsequently be explained, the outer detector 126 is at a first or reference electrical potential. The inner detector is utilized to search out and determine high points or low points with reference to the potential of the outer detector. The electrical probe described herein is, also, utilized to treat.

It should be noted with respect hereto that because of the independent biassing the inner and outer detectors can be independently or simultaneously moved.

As shown in FIG. 1, associated with the probe 22 is a ground assembly, generally, indicated at 148. The ground assembly comprises a metallic grasping member 150 which is held by the object to be treated, such as in a person's hand. The member 150 is electrically connected to the plug 20 through lead wire 152. The lead wire is soldered to a threaded member (not shown) which is threadably received by the member 150 through a suitable threaded bore (not shown) formed therewithin. The other end of the wire 152 is connected to the plug 120. The associated socket prong of the plug to which the wire 152 leads is connected to the grounding source of the power supply.

THE CIRCUITRY AND OPERATION OF THE DEVICE

The following briefly summarizes the circuitry employed with respect to the various energy applicators, as well as the mode of utilization.

A. The Light Probe

Figure 12:
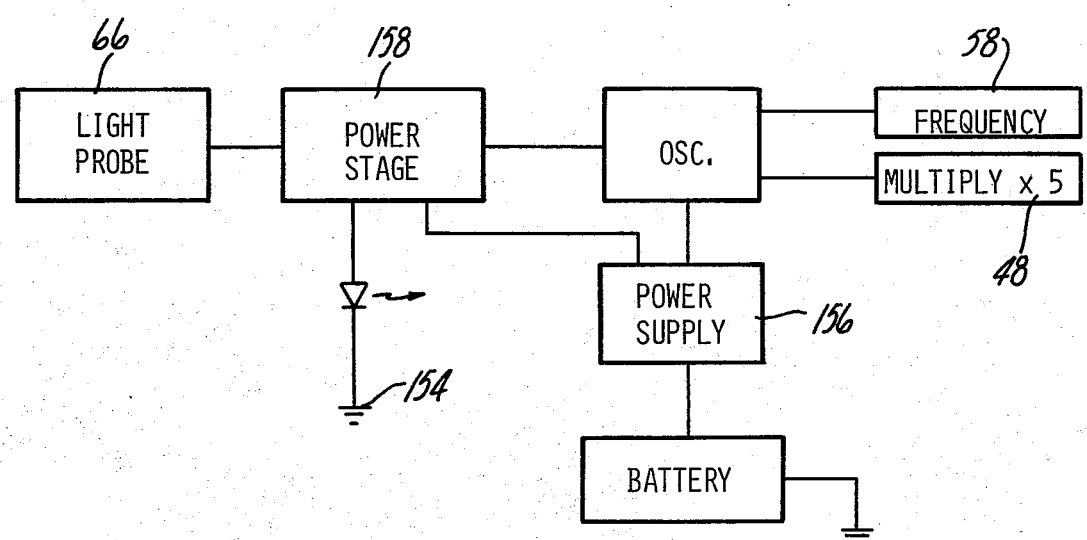
FIG. 12 is a block circuit diagram denoting the search and treatment circuitry for use with light energy.

In FIG. 12 there is depicted schematically the circuitry associated with the light probe function. The circuitry includes a power stage which is connected to the light probe through the appropriate plug and socket. The power stage is grounded as at 154. The power stage, per se, is a logic circuit comprising a plurality of integrated circuits. The power stage is powered from the power supply, which, in turn, derives its energy from the battery stored within the unit 10. An oscillator 156 is interposed between the power stage and the frequency selector 58 and is in electrical communication therebetween. The magnitude of the oscillations can be increased by a magnitude of five through the multiplier 48 in electrical communication therewith. The oscillator is, also, powered by the power supply.

In utilizing the light probe, the plug thereof is inserted into the appropriate socket. With the device turned on the light button 40 is depressed. At such time the output light should be illuminated. The probe is then moved along and in contact with or in proximity to the tissue to be explored. Any changes in auricular cardiac reflex as denoted by the probe are then fed to a suitable readout device (not shown) with records such differentials, or can be read manually be the practitioner. Thus, the light probe searches out the high points and low points.

B. The Magnetic Probe

In FIG. 13, there is depicted a schematic diagram of the circuitry employed with the magnetic probe 96. The probe which is utilized as a treatment probe is electrically connected to a current detector circuit which provides an output of either plus or minus, as dictated by the logic circuit associated therewith. The current detector is powered by the power stage 158, which, in turn, is supplied energy by the power supply 156. The power supply derives energy from the battery.

In addition, the power supply supplies electrical energy to the oscillator and the logic circuit.

Because the magnetic probe is unipolar safety indicators are incorporated herewith. More particularly, the probe is plugged into its appropriate socket. If the probe is properly functioning both the output lamp and the circuit complete lamps will illuminate. This is because the probe, as hereinbefore noted, utilizes two coils.

In treating with the probe, it is placed about one millimeter from the tissue area to be treated.

C. The Bipolar Electrical Probe

In FIGS. 10 and 11, there is depicted, respectively, the search circuit and treatment circuit for the bipolar electrical probe. The search circuit, as depicted in FIG. 10, comprises the three-way polarity switch 62 which is adjustable between plus, minus and plus-minus, The polarity of the output, as determined by the switch 62, is dictated by the power supply 156, which, as noted, is both plus, minus and plug-minus. The output terminal signal from the probe is supplied by the power supply which is a square wave function regardless of the polarity. The polarity switch is, also, electrically connected to a differential amplifier 160 which detects the polarity of the points being searched. The amplifier is powered by the power supply and is directed by the logic circuit 162 which comprises an integrated circuit. The electrical energy for the logic circuit is, also, provided by the power supply. Thus, the output of the logic circuit controls and dictates the differential amplifier. Additionally, the output of the logic circuit controls an audio means 64 which indicates, audio-wise the determination of a point.

In searching with the electrical probe, it is plugged into the device, with the user holding the member 150. The search button 40 and electrical button 40 are both depressed to actuate the logic circuit. The volume control 52 is turned all the way up; the sensitivity is turned to maximum with the polarity on positive. The probe is then placed at a predetermined point "O" of the body or the auricle (FIGS. 3 and 4). The sensitivity knob 56 is then rotated until the audio just goes off. It should be noted that the sensitivity is controlled by a level adjuster which is connected to the differential amplifier and, likewise controlled by the logic circuit. When the audio goes "off" the outer detector 126 is then set at reference zero. By further contacting the tissue with the probe points of imbalance, as a result of the differences between the electrical potential of the inner detector and the outer detector, are transmitted through the audio output.

In use the search conducted in positive polarity should be repeated in negative polarity with the same procedure.

After the point(s) to be treated has been determined, the sampe probe 22 is utilized to treat the point, by switching from the search mode to the treatment mode, which is achieved by disengaging the search button 40 on panel 38.

The present treatment mode includes a novel arrangement for indicating that treatment is being achieved. In FIG. 11 there is depicted the circuitry associated with the treatment mode of the bipolar electrical probe. The circuit employed herein includes a means for indicating that treatment is being effectuated and which is blocked out in FIG. 11 by the dash lines, and, generally, denoted at 166.

The entire treatment circuit is powered by the battery which supplies energy to the power supply 156 and the power stage 158. The frequency of the output of the power stage is dictated by the oscillator which is electrically connected to the frequency adjuster and the frequency multiplier. The rheostatic intensity variator 54 is interposed between the power stage and the probe 22. The duration of treatment is predetermined through the timer switch 60 which permits flow of electricity to the oscillator for a preselected amount of time.

Interposed between the probe 22 and the intensity control is the means for indicating that treatment is being effected or "circuit complete" 166. The circuit complete, generally, comprises an audio indicator 164, which is actuated by the logic circuit 162. The logic circuit, also, controls the circuit complete illuminating means 44 on panel 42. Thus, when treatment is being effectuated there is provided both a visual display and audio indication. The circuit complete also comprises the polarity switch 62 which dictates the polarity of the output of the power supply. The differential amplifier 160 is electrically connected to a current detector relay interposed between the polarity switch and the probe. Thus, upon the inner detector 128 and outer detector 126 contacting the tissue at the same frequency, there is relayed through the current detector to the logic circuit sufficient impulses to activate the illuminating means and the audio means. If the circuit is not completed, then the indicators will not function. Thus, the present invention provides means for indicating that electrical pulses are being transmitted into the tissue under treatment.

In utilizing rhe present apparatus, it is possible to treat any portion of the body, as well as the auricle. As shown in FIGS. 3 and 4, there is a correlation between the regions of the auricle and distinct portions of the torso. These correlations have been heretofore established by researchers in the field. In treating and searching out points of imbalance within any region, again, there is a correlation between the region searched and/or treated and the frequency at which treatment or searching is conducted. In FIG. 5 there is shown a conversion table which correlates FIGS. 3 and 4 to the required frequencies. Again, this interrelationship has been established by researchers.

In FIG. 14 there is depicted, schematically, the mode for indicating the status of the battery. This circuit is always on whenever the device 10 is activated. The battery status is dictated by supplying energy from the battery to the power supply, is actuated by depression of any search and/or energy-related pushbutton switch 40. The output of the logic circuit is connected to illuminating means 44 denoted as "battery good" or "charge battery" depending on the output signal of the logic circuit 168. Interposed between the power supply and the logic circuit is a differentiator and discriminator 170 which analyzes the nature of the output of the power supply to permit the proper functioning of the logic circuit. If the signal from the logic circuit indicates that the battery has a sufficient charge, then, the battery good illuminating means is activated. On the contrary, if the battery is weak, then, the "charge battery" illuminating means will be activated. Again, this circuit is always on when the device is being utilized. Also, depression of the "battery" pushbutton 40 will indicate the status of the battery.

In the event that the battery requires recharging, then this, also, can be accomplished by the present invention. Referring, now, to FIG. 15, there is depicted the circuitry associated with the battery recharging function. The recharging function utilizes an external battery charger 170 of conventional constructon which plugs into socket 64 on the housing, which is an interlock connecting to a logic circuit 172 which has its output, in turn, connected to the "battery charging" illumination means 44 and the battery to permit the flow of charge thereto. Interposed between the logic circuit 172 and the battery is a limiting resistor 174 which prevents overcharging of the battery. An override switch, namely, the multiplier switch 40 can be closed to override the resistor to speed up the recharging process.

Intermittent depression of the "battery" button switch 40 indicates the status of the battery to determine when recharging has been completed.

In utilizing the battery recharger the device is maintained in the "off" status, when the faster charge is required, both the multiplier and "off" buttons are depressed.

In deploying the present invention, it is noteworthy that points can be detected in either plus and minus. Furthermore, if a point is detected in both plus and minus, then, it is treated in plug-minus polarity. Also, in searching, minus or negative points can be detected in either negative or plus-minus polarity. Furthermore, the search function is carried out at low currents, over a range of from about two to ten microamps, to obviate potential hazards and for minute detection.

It is to be appreciated that there has been described herein a device for effecting an automatic transcutaneous affect through varying types of energy, and which is capable of detecting and treating points of imbalance to return a body to homostatius.

Having, thus, described the invention, what is claimed is:

1. A device for detecting and treating points of impedance imbalance in a warm blooded animal to effect an autonomic transcutaneous affect to the tissues of the body, comprising:
   (a) a housing,
   (b) a battery disposed in the housing,
   (c) a plural polarity power supply electrically connected to the battery,
   (d) a plurality of logic circuits electrically connected to the power supply and controlling plural forms of energy outputs, each of the logic circuits defining means for varying the output of the power supply into electrical, magnetic or light energy, each logic circuit having an output associated therewith, and
   (e) means associated with each of the associated logic circuits for applying the output of the logic circuits to the tissue area to have the affect applied thereto.

2. The device of claim 1 which further comprises:
   interlocking means disposed on the housing for the logic circuits such that only one logic circuit is operable at one time.

3. The device of claim 2 which further comprises:
   a plurality of illumination means disposed on the housing and each illumination means being in electrical communication with one of the logic circuits for displaying the actuated logic circuit.

4. The device of claim 1 which further comprises:
   (a) means for varying the intensity of the outputs of the logic circuits;
   (b) means for varying the frequency of the outputs, and
   (c) means for changing the polarity of the output of the power supply,
   each of the means having an external control knob mounted on the exterior of the housing.

5. The device of claim 1 which comprises: at least three logic circuits and wherein:
   (a) one of the logic circuits controls an output of magnetic energy,
   (b) one of the logic circuits controls and output of bipolar electrical energy, and
   (c) one of the logic circuits controls an output of light energy.

6. The device of claim 5 which further comprises:
   means for indicating that treatment of bipolar electrical energy is being effected, said means comprising:
   a logic circuit,
   a differential amplifier electrically connected to the logic circuit,
   a polarity switch for altering the polarity of the output of the power supply and being electrically connected to the differential amplifier, the power supply and the means for applying the output of the circuit, and
   an illumination means disposed on the housing and connected to the logic circuit, the illumination means displaying the functioning of the means for indicating.

7. The device of claim 6, which further comprises:
   means for emitting an audible sound interconnected to the electrical energy controlling logic circuit for indicating that the means for applying the output thereof to the tissue is functioning, when in the treatment mode.

8. The device of claim 5 wherein the means for applying the magnetic output comprises:
   (a) a housing,
   (b) an elongated magnetic pin extending through the housing and having a portion thereof disposed exteriorly of the housing,
   (c) a pair of coils wound in opposite direction around the pin, the coils being disposed in the housing,
   (d) means for electrically interconnecting the coils to the associated logic circuit.

9. The device of claim 5 wherein the means for applying the electrical output comprises:
   (a) a housing having a first end and a second end, an aperture being formed in the first end;
   (b) a pair of concentric detecting pins disposed in the housing and extending through the aperture,
   (c) biassing means for each of the pins such that each pin can be independently retracted into the housing, the biassing means normally urging the pins through the aperture, and
   (d) means electrically interconnecting the pins to the associated logic circuit.

10. The device of claim 5 wherein the means for applying the output of the light energy circuit comprises:
    a light emitting diode in electrical communication with the associated logic circuit.

11. The device of claim 1 which further comprises:
    a timing means for timing the output of any logic circuit.

12. The device of claim 1 which further comprises:
    means for recharging the battery.

* * * * *